US008236253B2

(12) United States Patent
Coyle et al.

(10) Patent No.: US 8,236,253 B2
(45) Date of Patent: Aug. 7, 2012

(54) PORTABLE STERILIZING APPARATUS FOR SURGICAL AND DENTAL INSTRUMENTS

(75) Inventors: Michael J. Coyle, Huber Heights, OH (US); Ronald A. Gatchell, Tipp City, OH (US); Richard L. Jones, Eaton, OH (US); Philip Marc Stewart, Greenville, OH (US); James E. Clapp, Tipp City, OH (US); Dennis L. Harris, Celina, OH (US)

(73) Assignee: Midmark Corporation, Versailles, OH (US)

( * ) Notice: Subject to any disclaimer, the term of this patent is extended or adjusted under 35 U.S.C. 154(b) by 1048 days.

(21) Appl. No.: 12/112,716

(22) Filed: Apr. 30, 2008

(65) Prior Publication Data

US 2008/0299003 A1    Dec. 4, 2008

Related U.S. Application Data

(60) Provisional application No. 60/914,884, filed on Apr. 30, 2007.

(51) Int. Cl.
*A61L 2/00* (2006.01)
(52) U.S. Cl. .......................................... 422/297; 422/296
(58) Field of Classification Search .................. 422/296, 422/297
See application file for complete search history.

(56) References Cited

U.S. PATENT DOCUMENTS

| | | |
|---|---|---|
| 4,145,279 A | 3/1979 | Selby, III |
| 4,238,447 A | 12/1980 | Wolff |
| 4,263,258 A | 4/1981 | Kalasek |
| 4,304,996 A | 12/1981 | Blades |
| 4,441,724 A | 4/1984 | Taylor |
| 4,755,292 A | 7/1988 | Merriam |
| 4,759,909 A | 7/1988 | Joslyn |
| 4,808,377 A | 2/1989 | Childers et al. |
| 4,865,814 A | 9/1989 | Childress |
| 4,872,563 A | 10/1989 | Warder et al. |
| D305,261 S | 12/1989 | Hobbs |
| 4,891,910 A | 1/1990 | Cook et al. |
| 4,892,705 A | 1/1990 | Sternfeld et al. |
| 4,892,706 A | 1/1990 | Kralovic et al. |
| 4,900,519 A | 2/1990 | Nichols |
| 4,909,988 A | 3/1990 | Childers et al. |

(Continued)

OTHER PUBLICATIONS

VWR Lab Shop, VWR Sterilizers, Model AS12 [online], [retrieved Apr. 24, 2009]. Retrieved from the Internet: <URL: http://vwrlabshop.com/vwr-sterilizers-model-as12/p/0013004/.

(Continued)

*Primary Examiner* — Kevin Joyner
(74) *Attorney, Agent, or Firm* — Wood, Herron & Evans, LLP

(57) ABSTRACT

A portable steam sterilizer for surgical instruments includes a tray configured to hold the instruments and a pressure chamber. The pressure chamber includes a cavity portion and a handle portion. The cavity portion includes a set of walls and is configured to releasably receive the tray, while the handle portion is coupled to the tray for selectively inserting and removing the tray respectively into and from within the cavity portion. The handle portion is sealingly engageable with the cavity portion to thereby define the pressure chamber. A steam inlet fluidly communicates the pressure chamber with a source of steam to selectively permit steam to flow from the source of steam and into the pressure chamber. A steam outlet fluidly communicates the pressure chamber with a steam management assembly to selectively permit steam to flow from the pressure chamber and into the steam management assembly.

18 Claims, 12 Drawing Sheets

U.S. PATENT DOCUMENTS

| | | | |
|---|---|---|---|
| 4,932,160 | A | 6/1990 | Sperko |
| D312,745 | S | 12/1990 | Daenen et al. |
| 5,068,085 | A | 11/1991 | Hastings |
| 5,098,676 | A | 3/1992 | Brooks, Jr. |
| 5,132,084 | A | 7/1992 | Harrell et al. |
| 5,146,713 | A | 9/1992 | Grafius |
| 5,195,790 | A | 3/1993 | Bulko et al. |
| 5,223,229 | A | 6/1993 | Brucker |
| 5,234,124 | A | 8/1993 | Buckner, II et al. |
| 5,249,392 | A | 10/1993 | Houston et al. |
| 5,252,303 | A | 10/1993 | Goof |
| 5,256,382 | A | 10/1993 | Ford et al. |
| 5,258,921 | A | 11/1993 | Ellis |
| 5,261,250 | A | 11/1993 | Missimer |
| 5,266,275 | A | 11/1993 | Faddis |
| 5,271,893 | A | 12/1993 | Newman |
| 5,290,511 | A | 3/1994 | Newman |
| D347,696 | S | 6/1994 | Tominaga |
| 5,366,693 | A | 11/1994 | Burgos et al. |
| 5,390,322 | A | 2/1995 | O'Brien et al. |
| 5,407,648 | A | 4/1995 | Allen et al. |
| 5,424,047 | A | 6/1995 | Zwingenberger et al. |
| 5,424,048 | A | 6/1995 | Riley |
| 5,520,892 | A * | 5/1996 | Bowen .................. 422/295 |
| 5,535,141 | A | 7/1996 | Lussi |
| 5,540,901 | A | 7/1996 | Riley |
| 5,566,508 | A | 10/1996 | Houston |
| 5,571,476 | A | 11/1996 | Newman |
| 5,713,941 | A | 2/1998 | Robins et al. |
| 5,730,944 | A | 3/1998 | Peake |
| 5,761,069 | A | 6/1998 | Weber et al. |
| 5,858,304 | A | 1/1999 | Breach |
| 5,868,999 | A | 2/1999 | Karlson |
| 5,880,438 | A | 3/1999 | Parrini et al. |
| 5,882,612 | A | 3/1999 | Riley |
| 5,906,801 | A * | 5/1999 | Goughnour .................. 422/300 |
| 5,993,754 | A | 11/1999 | Lemmen et al. |
| 6,007,780 | A | 12/1999 | Heredia |
| 6,017,105 | A | 1/2000 | Goughnour et al. |
| 6,048,502 | A | 4/2000 | Easter |
| 6,048,503 | A | 4/2000 | Riley et al. |
| 6,058,247 | A | 5/2000 | Lahey et al. |
| D432,205 | S | 10/2000 | Tien Lin |
| 6,217,835 | B1 | 4/2001 | Riley et al. |
| 6,251,345 | B1 | 6/2001 | Palmers |
| 6,319,479 | B1 | 11/2001 | Houston |
| 6,323,032 | B1 | 11/2001 | Kuepper et al. |
| 6,391,258 | B1 | 5/2002 | Peake et al. |
| 6,416,144 | B1 | 7/2002 | Houston et al. |
| 6,589,477 | B1 | 7/2003 | Frieze et al. |
| 6,713,029 | B1 | 3/2004 | Krafft et al. |
| 6,793,900 | B1 | 9/2004 | Morck et al. |
| 6,874,634 | B2 | 4/2005 | Riley |
| 6,984,359 | B2 | 1/2006 | Florkey et al. |
| 6,992,494 | B2 | 1/2006 | Kaiser et al. |
| D516,222 | S | 2/2006 | Mills |
| 7,435,398 | B2 * | 10/2008 | Lund-Jensen et al. ........ 422/298 |
| 2002/0085945 | A1 | 7/2002 | Florkey et al. |
| 2002/0098139 | A1 | 7/2002 | Sparks |
| 2003/0118491 | A1 | 6/2003 | Frieze et al. |
| 2003/0200876 | A1 | 10/2003 | Brokaw et al. |
| 2004/0042943 | A1 | 3/2004 | Wanselin |
| 2004/0091389 | A1 | 5/2004 | Malkin et al. |
| 2004/0256269 | A1 | 12/2004 | Gleichauf et al. |
| 2005/0001634 | A1 | 1/2005 | Kaiser et al. |
| 2005/0050644 | A1 | 3/2005 | Severns et al. |
| 2005/0063883 | A1 | 3/2005 | Sullivan |
| 2005/0191207 | A1 | 9/2005 | Terwilliger et al. |
| 2005/0263421 | A1 | 12/2005 | Kohler |
| 2005/0263422 | A1 | 12/2005 | Kohler |
| 2006/0251540 | A1 | 11/2006 | Benning et al. |

OTHER PUBLICATIONS

Paragon Medical, Pelton Crane Delta XL Autoclave [online], p. 2, [retrieved Apr. 24, 2009]. Retrieved from the Internet: <URL: http://www.paragonmed.com/autoclave.shtml.

DRE, Statim Sterilizer [online], [retrieved May 21, 2009]. Retrieved from the Internet: <URL: http://www.dremed.com/catalog/documents/sci-can.

SciCan, Statim Sterilizer [online], [retrieved May 21, 2009]. Retrieved from the Internet: <URL: http://www.piercing.org/statim/index.htm.

ALFA Medical, Scican Statim 2000 Parts, main view [online], [retrieved May 21, 2009]. Retrieved from the Internet: <URL: http://www.autoclave-parts.com/Z-Scican/Statim-2000/Statim-2000.html.

ALFA Medical, Scican Statim 2000 Sterilizer Parts, right view [online], [retrieved May 21, 2009]. Retrieved from the Internet: <URL: http://www.autoclave-parts.com/Z-Scican/Statim-2000/Statim-2000-right.html.

Internet advertisement for VWR Sterilizer, dated May 9, 2006.

Internet website page disclosing a Pelton Crane Delta XL Model Sterilizer, dated May 9, 2006.

Internet website page showing a Statim Sterilizer kit.

* cited by examiner

PORTABLE STERILIZING APPARATUS FOR SURGICAL AND DENTAL INSTRUMENTS

CROSS-REFERENCE TO RELATED APPLICATIONS

This application claims priority to U.S. Provisional Application No. 60/914,884, filed Apr. 30, 2007, the disclosure of which is hereby incorporated herein by reference in its entirety. This application is related to the following U.S. Patent Applications all filed on even date herewith, the disclosures of which are incorporated by reference herein: U.S. patent application Ser. No. 12/112,685, filed Apr. 30, 2008 ; U.S. patent application Ser. No. 29/317,451, filed Apr. 30, 2008 (now U.S. Pat. No. D598,564); and U.S. patent application Ser. No. 29/317,452, filed Apr. 30, 2008 (now U.S. Pat. No. D603,053). The entire disclosures of these U.S. patent applications are incorporate into this application by reference.

TECHNICAL FIELD

The invention relates to sterilizers and, more particularly, to portable or table-top steam-based sterilizers for surgical and dental instruments.

BACKGROUND

In the medical and dental fields, it is desirable to provide relative quick sterilizing of surgical instruments and the like. Many systems commonly use steam to provide this requisite sterilization. Some of these systems, however, require large spaces and are cumbersome to transport.

To address this issue, portable or "table-top" systems, such as one described in U.S. Pat. No. 5,271,893, have been developed. Such systems may include a portable holding device configured to receive a removable sealable pressure vessel. Steam is then injected by other portions of the device into the pressure vessel to carry out the sterilization of instruments held by the vessel. There are drawbacks, however, present in devices of this type. For example, insertion and removal of the vessel into the holding device may require alignment of corresponding connectors on the vessel and the other portions. These connectors may include those providing entry and evacuation of steam respectively into and from the vessel. Alignment of the connectors may not always be easily achieved, thereby leading to bending and damaging of the connectors. Such damage reduces the life expectancy of the vessel and/or holding device.

Another drawback of devices of the type described above lies in the relatively complex access to the sterilized tools and instruments held by the vessel. Access may, for example, require a two-hand operation to disassemble portions and access an interior portion. Access may further require a relatively large space on a table surface or the like to support the two portions once they have been separated.

Yet another drawback of devices of the type described above relates to replacement of a seal or gasket intended to prevent steam from escaping the vessel. Devices of this type may include a thin, elongate gasket tightly retained in a channel on an interior surface of the vessel. When a user determines that the gasket needs replacement, replacement requires a somewhat complex and/or time-consuming procedure to remove the gasket from the channel and subsequently insert a new one.

Moreover, known devices of the type described above may need to accept vented cassettes that a specific set of instruments, such that instruments required for a particular use can be sterilized and kept together. Cassettes may be vented via apertures on opposed top and bottom walls as well as on opposed lateral walls, such that steam can flow multidirectionally into and out of the cassettes. Conventional devices, however, may provide an inadequate flow of steam into the cassettes. These devices may, for example, provide a very close fit between the cassette and the vessel holding it, such that flow of steam is only permitted through the apertures on the top and bottom walls, while not through the apertures on the lateral walls.

A portable steam sterilizing device capable of accepting and sterilizing surgical instruments and cassettes in an improved manner is therefore desirable.

Moreover, a portable steam sterilizing device that provides simpler access to the sterilized instruments and fewer maintenance considerations is similarly desirable.

SUMMARY

In accordance with an embodiment of the invention, a portable steam sterilizer for surgical instruments includes a tray configured to hold the instruments and a pressure chamber. The pressure chamber includes a cavity portion and a handle portion. The cavity portion includes a set of walls and is configured to releasably receive the tray, while the handle portion is coupled to the tray for selectively inserting and removing the tray respectively into and from within the cavity portion. The handle portion is sealingly engageable with the cavity portion to thereby define the pressure chamber.

A steam inlet fluidly communicates the pressure chamber with a source of steam to selectively permit steam to flow from the source of steam and into the pressure chamber. A steam outlet fluidly communicates the pressure chamber with a steam management assembly to selectively permit steam to flow from the pressure chamber and into the steam management assembly.

In one embodiment, the pressure chamber may include a resilient gasket member releasably coupled to the handle portion, sealingly engageable with the cavity portion, and configured to prevent steam from flowing out of the pressure chamber. The gasket member may include a channel configured to deform when filled with steam to thereby bring the handle portion into sealing engagement with the cavity portion. The portable steam sterilizer may further be releasably coupled to the tray.

In another aspect of this invention, a sterilizer may include a main housing further including a thermal insulation assembly. The thermal insulation assembly is disposed to contact at least one of the walls of the pressure chamber to frictionally hold it within the housing. The main housing may also include at least two walls interconnected by fasteners.

A heating element may be disposed on an outer face of at least one of the walls of the pressure chamber. The heating element may be configured to dry an interior portion of the pressure chamber when a substantial portion of the steam has been evacuated from the pressure chamber at about an end of a sterilizing cycle. The heating element may be further configured to dry the interior portion when the handle portion is decoupled from the cavity portion and be also configured to create a positive pressure flow from the interior portion.

A sterilizer may include a motorized locking assembly configured to hold the handle portion in sealing engagement with said cavity portion. The locking assembly may include an elongate locking element extending laterally from the handle portion, as well as a motor operatively coupled to an engaging member configured to engage the elongate locking element. A sensor assembly may be operatively coupled to the locking assembly and be configured to detect a position of the handle portion to thereby permit actuation of the locking assembly.

In another aspect of this invention, a sterilizer may include a tray having at least one generally, vertically-oriented wall and that includes a first set of apertures configured to let steam flow therethrough. The tray is configured to hold a surgical instrument cassette thereon, and which includes a second set of walls and a second set of apertures disposed on at least one of the walls of the second set. Apertures of the second set are configured to let steam flow therethrough. The apertures of the first set are configured such that a flow of steam is not substantially hindered through the apertures of the second set.

In another embodiment, a pressure chamber for use within a portable steam sterilizer for surgical instruments includes a cavity portion and a handle portion. The cavity portion includes a set of walls and is configured to releasably receive a tray holding the instruments. The handle portion is sealingly engageable with the cavity portion to thereby define the pressure chamber.

The pressure chamber further includes a steam inlet and a steam outlet. The steam inlet is adapted for fluidly communicating the pressure chamber with a source of steam to selectively permit steam to flow from the source of steam into the pressure chamber. The steam outlet is adapted for fluidly communicating the pressure chamber with a steam management assembly to selectively permit steam to flow from the pressure chamber into the steam management assembly. In one aspect of this embodiment, the handle portion is configured to releasably couple to the tray.

In yet another embodiment, a method of sterilizing surgical instruments includes receiving the instruments on a tray coupled to a handle portion of a pressure chamber. The tray is received within a cavity portion of the pressure chamber. The handle portion is brought into sealing engagement with the cavity portion to thereby define the pressure chamber and steam is received within the pressure chamber to sterilize the instruments.

The method may further include evacuating steam from the pressure chamber; and drying an interior portion of the pressure chamber with heat selectively transferred into the pressure chamber. The method may also include inducing a positive flow of pressure from the pressure chamber.

Advantageously, by including a tray vented on the bottom and side walls, a portable steam sterilizing device in accordance with embodiments described herein provides adequate, multidirectional flow of steam from the pressure chamber and into and out of a cassette holding surgical instruments and the like.

Moreover, by including a tray that is separable from the pressure chamber, the portable steam sterilizer device in accordance with embodiments described herein provides simplified access to instruments held thereon. In another advantageous aspect of certain embodiments, by including a fixed steam inlet and a fixed outlet, the device has an improved life expectancy over known devices of the prior art that may include connectors that require alignment during insertion or removal of an instrument-holding vessel.

Similarly, the one-piece, removable gasket of some embodiments that is coupled to the handle portion, provides a less complex and less time-consuming gasket-replacement procedure than available with known devices.

BRIEF DESCRIPTION OF THE DRAWINGS

These and other objectives and advantages will become readily apparent to those of ordinary skill in the art from the following description of embodiments of the invention and from the drawings in which.

DETAILED DESCRIPTION

Figure 1:
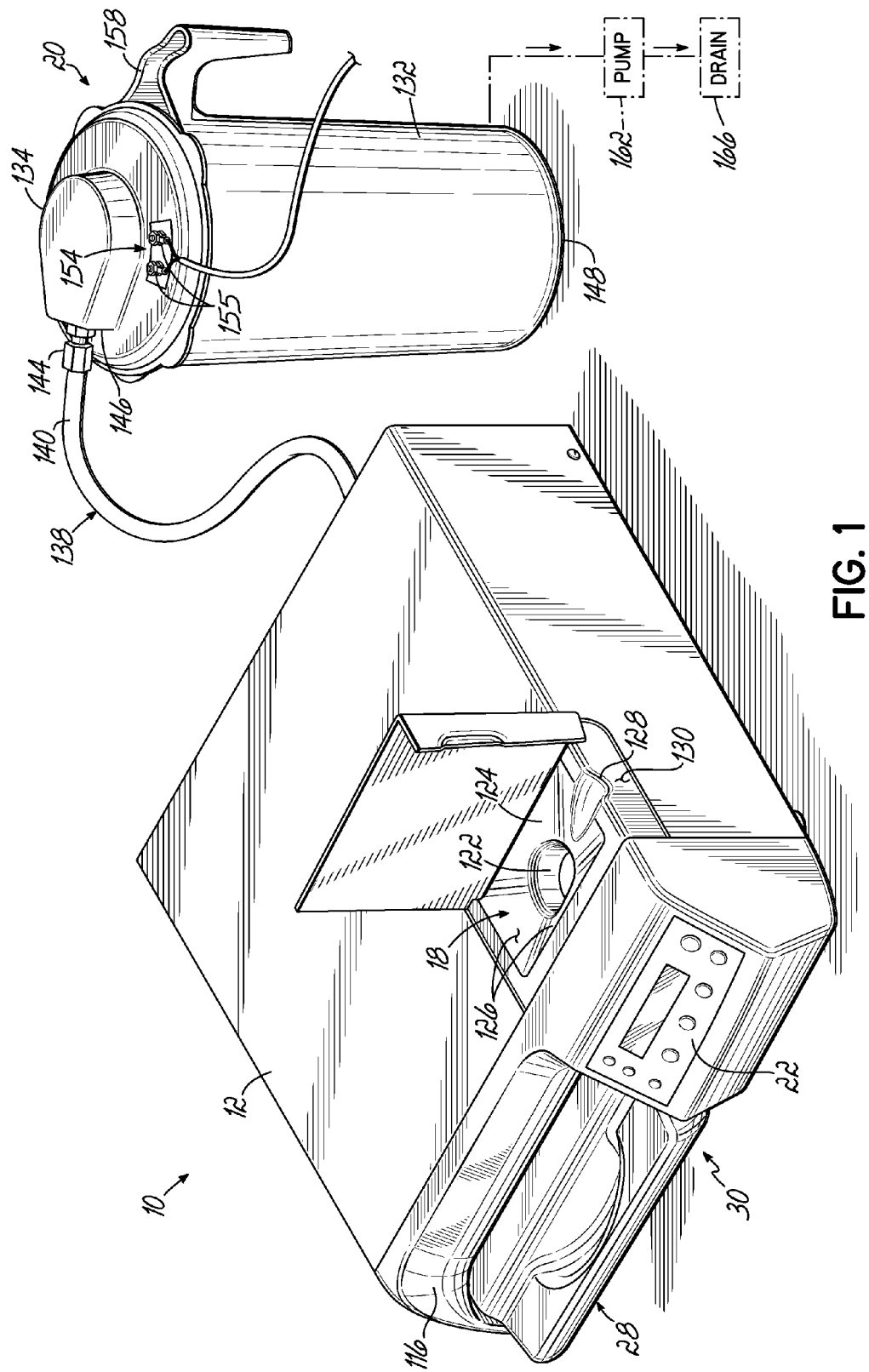
FIG. 1 is a perspective view of a portable steam sterilizer. in accordance with the principles of the present invention.

With reference to the figures, and more particularly to FIGS. 1-4, a portable steam sterilizer 10 includes an outer casing 12 within which a pressure chamber 14 is partially disposed. The steam sterilizer 10 further includes a steam management assembly 16, a water reservoir 18, an external condensation container or tank 20, and a control panel 22 for providing input into the operation of the sterilizer 10 controlled by a control module 24.

The pressure chamber 14 includes a handle portion 28 defining a portion of the front face 30 of the sterilizer 10. The handle portion 28 is coupled to a tray 32 configured to hold instruments such as surgical or dental instruments that require sterilizing.

Figure 2:
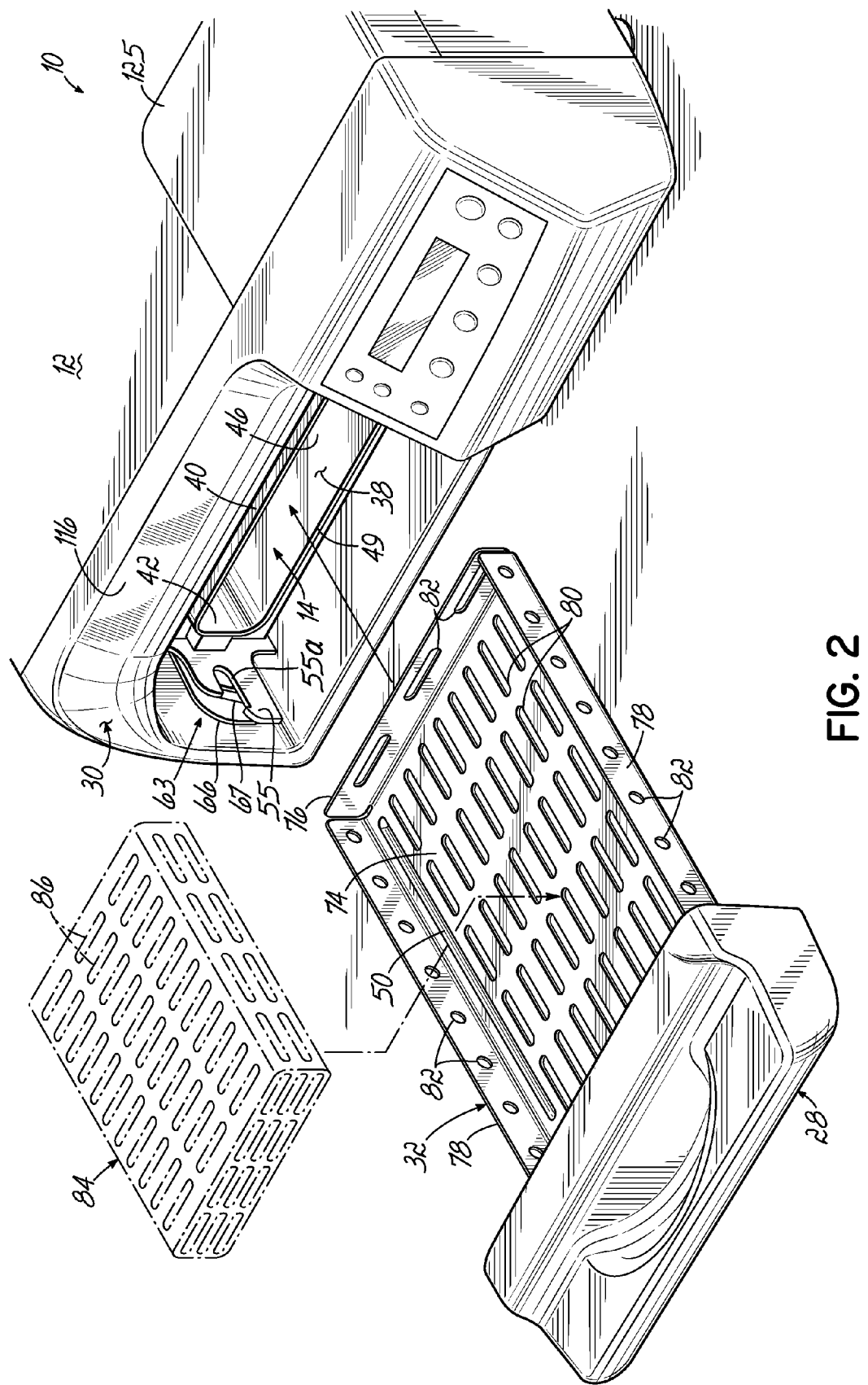
FIG. 2 is a partial perspective view of the sterilizer of FIG. 1, including a tray and a handle portion coupled thereto.
Figure 3:
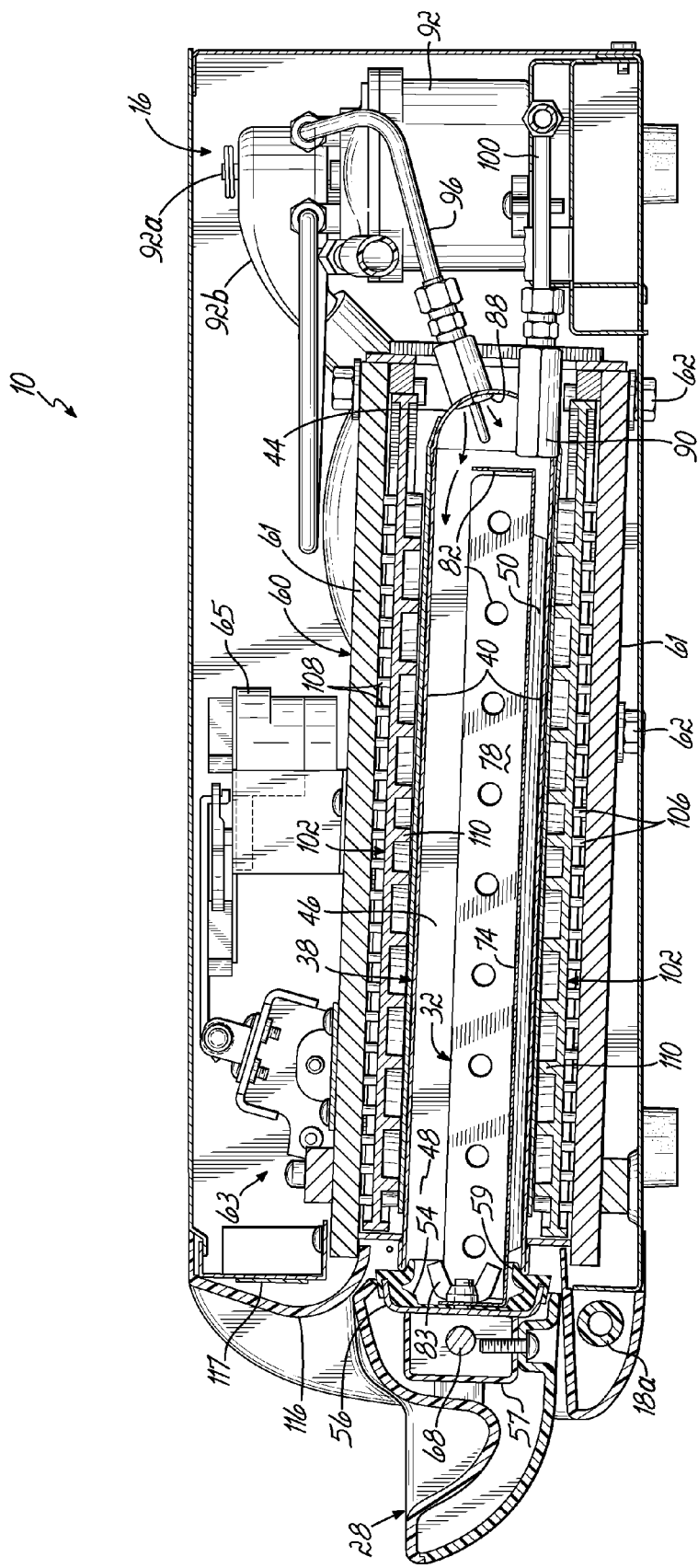
FIG. 3 is a partial cross-sectional elevational view of the sterilizer of FIG. 1.
Figure 3A:
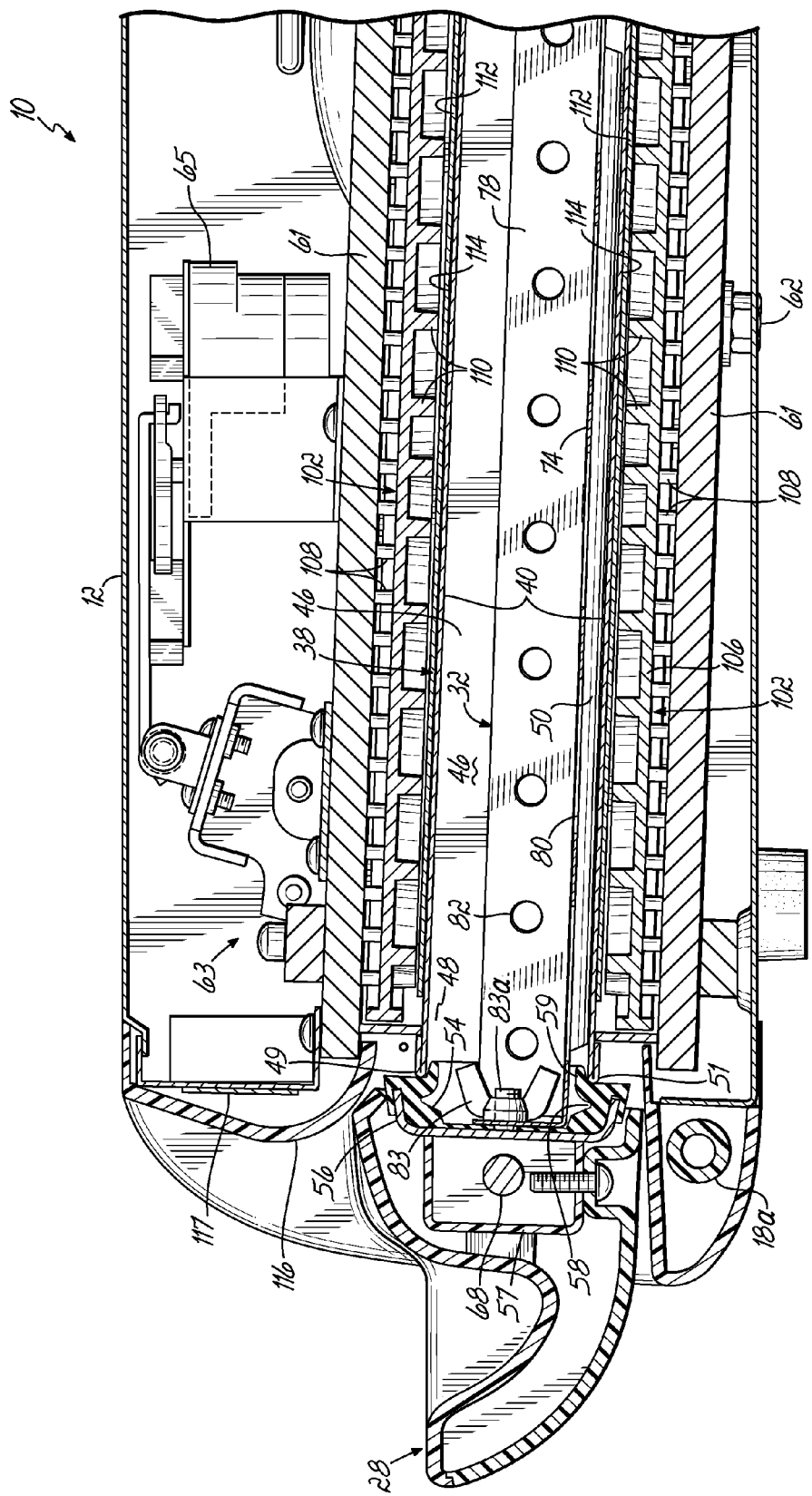
FIG. 3A is an enlarged elevation view of a front section the sterilizer of FIGS. 1-3.

With reference to FIGS. 2-3A, the pressure chamber 14 includes a cavity portion 38 that is fixedly disposed within the outer casing 12 and which includes walls defining the overall shape of the cavity portion 38. The cavity portion 38, in the exemplary embodiment of FIGS. 2-3A, includes opposed, parallel top and bottom walls 40, opposed sidewalls 42 orthogonal to the top and bottom walls 40, and a rear wall 44, all of which jointly define such shape. In this exemplary embodiment, moreover, the walls 40, 42, 44 are integrally formed. It is contemplated that the cavity portion 38 may alternatively include suitably intercoupled walls such that steam can be retained in an interior portion 46 of the pressure chamber 14.

The walls 40, 42, 44 of the cavity portion 38 are made of a suitably chosen material such as, and without limitation, stainless steel, such that the integrity of the pressure chamber can be maintained during a sterilizing cycle even when under high internal steam pressure. In the exemplary embodiment of FIG. 2-3A, the walls 40, 42, 44 are made of stainless steel of having a thickness of about 0.036 inches. As described below, the thickness of one or more of the walls 40, 42, 44 is further suitably chosen to minimize the overall mass of the cavity portion 38, such that heat can be effectively conductively transferred from one or more heating elements disposed on one or more outside surfaces of the walls 40, 42, 44.

The cavity portion 38 includes an opening 48 such that the open-top tray can be inserted into and removed from the cavity portion 38. To facilitate the insertion and removal of the tray 32, one or more of guides may be suitably disposed along one or more of the walls 40, 42, 44 of the cavity portion 38 or as part of the tray 32. In the exemplary embodiment of FIGS. 2-3A, two sliding guides 50 are formed along the bottom plate 74 of the tray 32 and protrude therefrom to engage corresponding portion within the cavity portion 38 of the pressure chamber 14 such that the top tray can be slidably received by the cavity portion 38. Persons of ordinary skill in the art will readily appreciate that guides of any shape, dimensions, number and location may substitute the sliding guides 50. Alternatively, the sterilizer 10 may include no sliding guides at all. Similarly, a pair of gripping members, or tusks 55, restrict the position of the tray 32 once inserted into the cavity portion 38. More particularly, each of the tusks 55 includes a generally horizontally-oriented slot 55a that slidably receives a locking element 68, as explained below, that is connected to the handle portion 28. The lateral position of the tusks 55 further restricts lateral movement of the tray 32 and handle portion 28 coupled thereto.

With reference to FIGS. 1-3B, the pressure chamber 14, as described above, further includes a handle portion 28, which engages the cavity portion 38 at the opening 48 to thereby complete the pressure chamber 14. In this exemplary embodiment, the handle portion 28 defines a sixth wall of a six-wall pressure chamber 14. The handle portion 28 is thus slidably received within and is further sealingly engageable with the cavity portion 38 such that pressurized steam can be held within the pressure chamber 14 to effect the sterilization of the instruments held in the tray 32. To further facilitate the sealing engagement of the handle and cavity portions 28, 38, a seal or gasket member 54 is disposed about the opening 48 to the cavity portion 38.

The gasket member 54 is a resilient structure suitable to provide sealing against the potential flow of steam from within the chamber 14, especially along junctions between the handle and cavity portions 28, 38. In the exemplary embodiment of FIG. 3B, the gasket member 54 is made of a resilient material such as, and without limitation, rubber or composite materials, and is further rectangularly shaped such that it closely matches the shape of the opening 48. In this exemplary embodiment, furthermore, the gasket member 54 includes a slot 53 that engages a lip 56, partially defining a block support 57 of the handle portion 28, to facilitate engagement therewith. Other types of engagement between the handle portion 28 and gasket member 54 are contemplated, so long as they provide releasable intercoupling to facilitate replacement of the gasket member 54 if and when necessary. For example, and without limitation, one or more fasteners or clamps (not shown) may be used to hold the gasket member 54 in engagement with the block support 57 or any other portion of the handle portion 28.

Figure 3B:
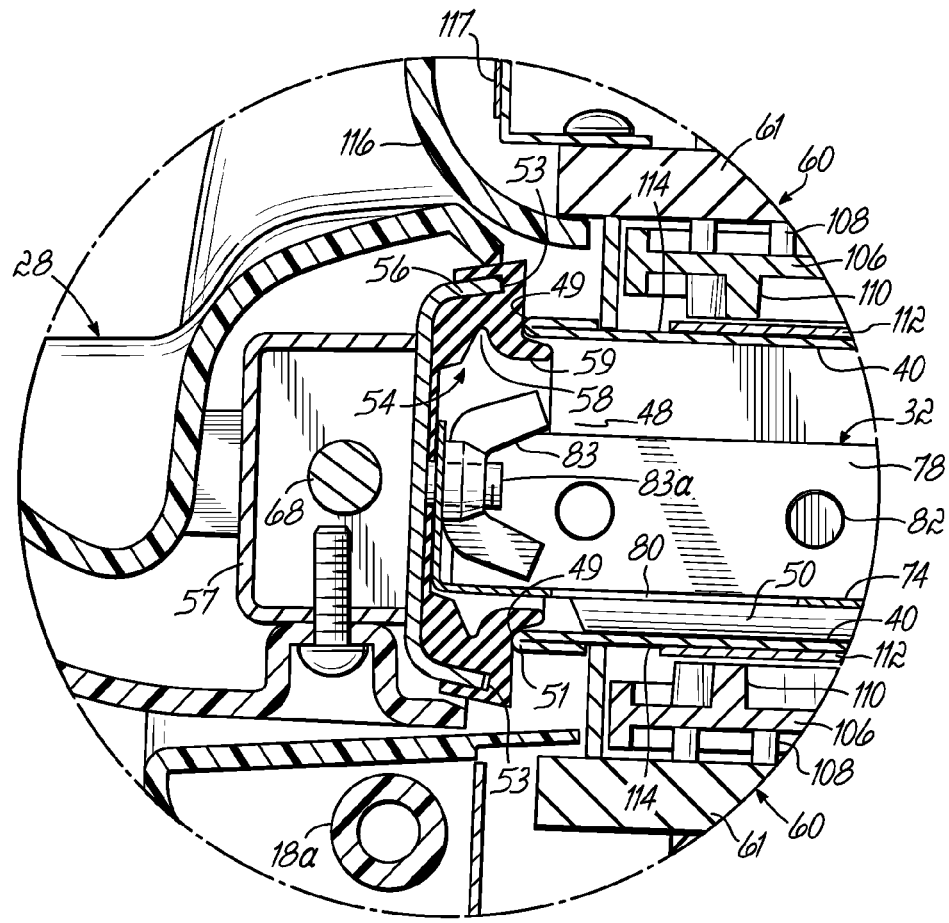
FIG. 3B is an enlarged elevation view of a handle portion of the sterilizer of FIGS. 1-3.

With continued reference to FIG. 3B, the gasket member 54 includes a channel or depression 58 adapted to expand when filled with pressurized steam within the pressure chamber 14, such that a flap portion 59 of the gasket member 54 is urged against an edge 49 of the opening 48 of the cavity portion 38. The edge 49 is non-abrasive to minimize damage to the gasket member 54. As best appreciated in FIG. 3B, the exemplary edge 49 has a U-shape defined by folded ends of the walls 40, 42 defining the cavity portion 38 such that the gasket member 54 is in contact with the non-abrasive folded section 51 of the U-shaped edge 49.

With reference to FIGS. 3-3B, the steam sterilizer 10 includes a main housing 60 that holds the cavity portion 38 therein and provides structural integrity to the pressure chamber 14, especially when pressurized steam fills the chamber 14. As explained below, the housing 60 frictionally restricts the translational movement of the cavity portion 38 and further restricts the pressurized steam-induced expansion of the pressure chamber 14. The housing 60 is defined by walls 61 in the form of solid plates made, for example, of metal. Two or more of the walls 61 are joined via fasteners such as bolts 62, thereby facilitating assembly of the housing 60 as well as disassembly thereof if and when necessary, for example, for maintenance purposes.

Figure 4:
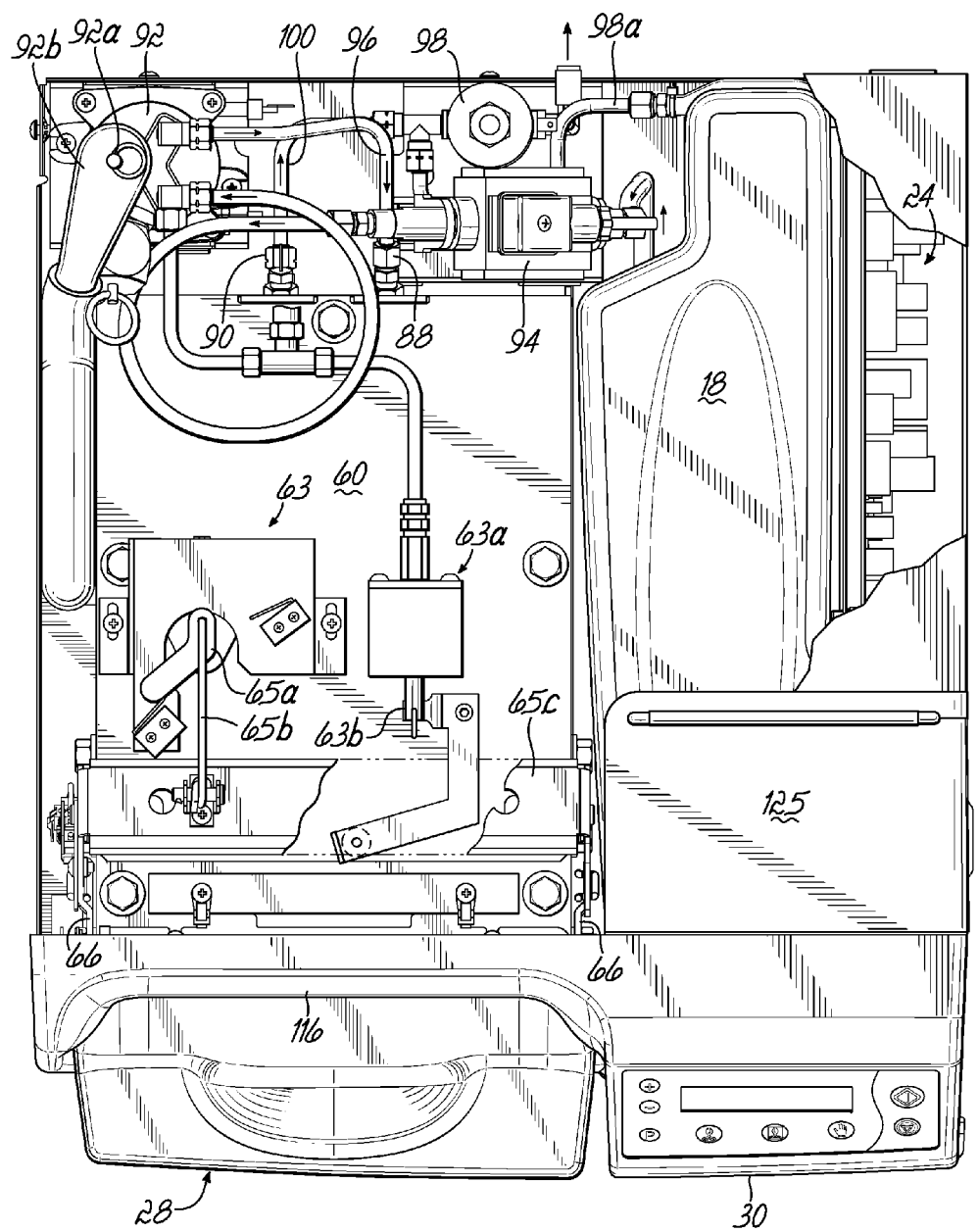
FIG. 4 is a top view of the sterilizer of FIGS. 1-3.
Figure 5A:
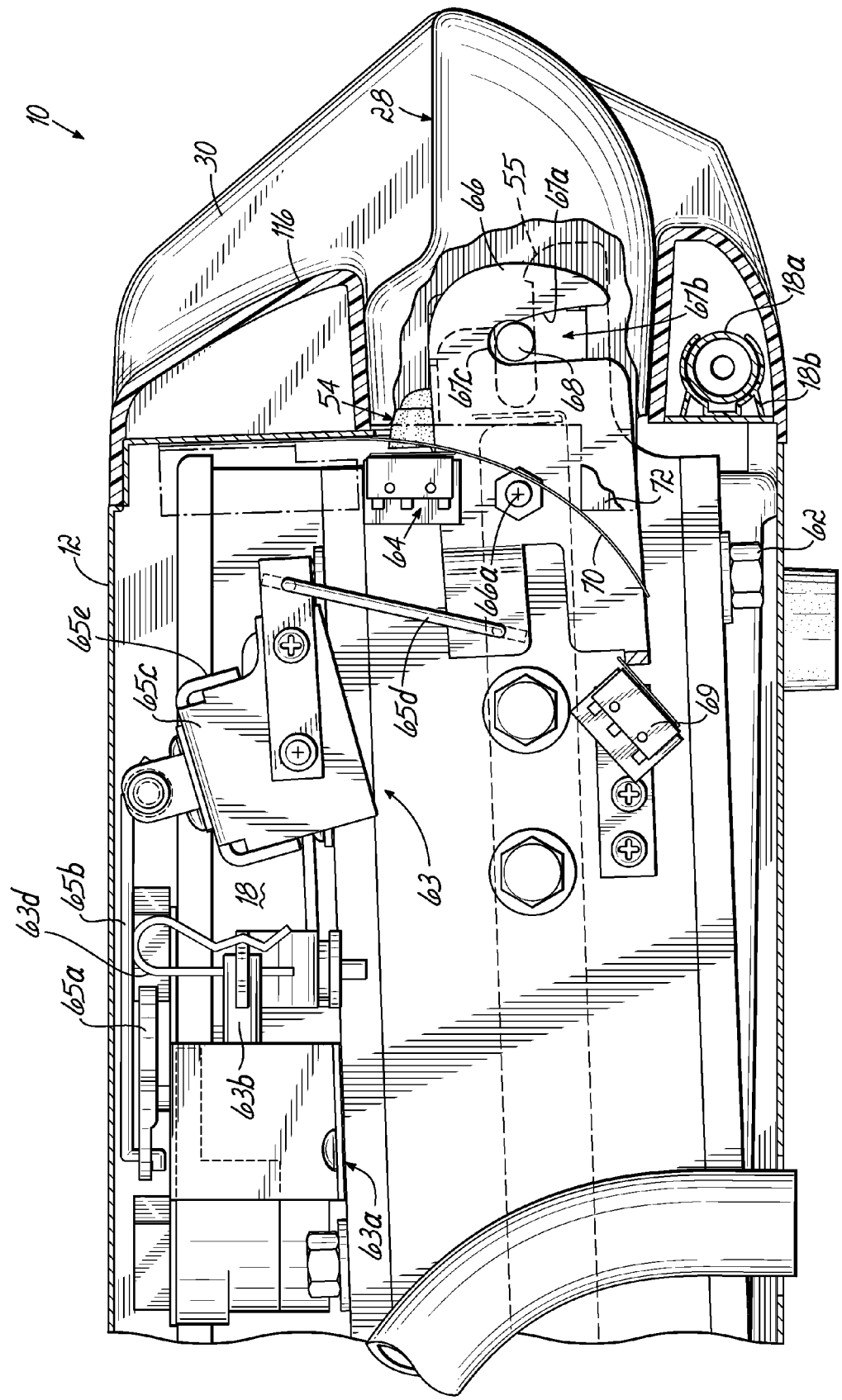
FIG. 5A is a partial cross-sectional elevational view of the sterilizer of FIGS. 1-3, taken from a left side of the sterilizer.
Figure 5B:
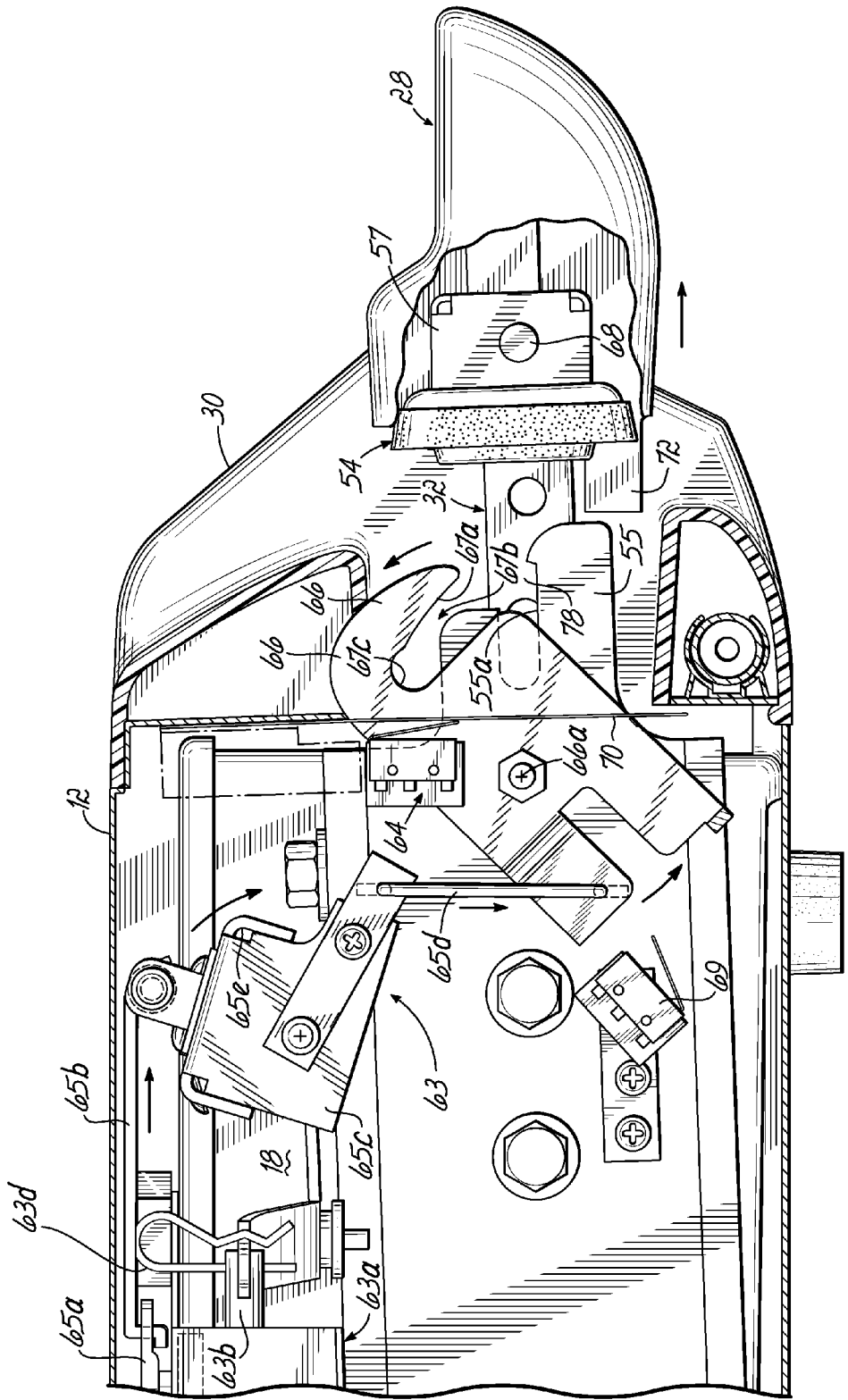
FIG. 5B is an enlarged partial cross-sectional view of a front section of the sterilizer of FIGS. 1-3, taken from the left side of the sterilizer.
Figure 5C:
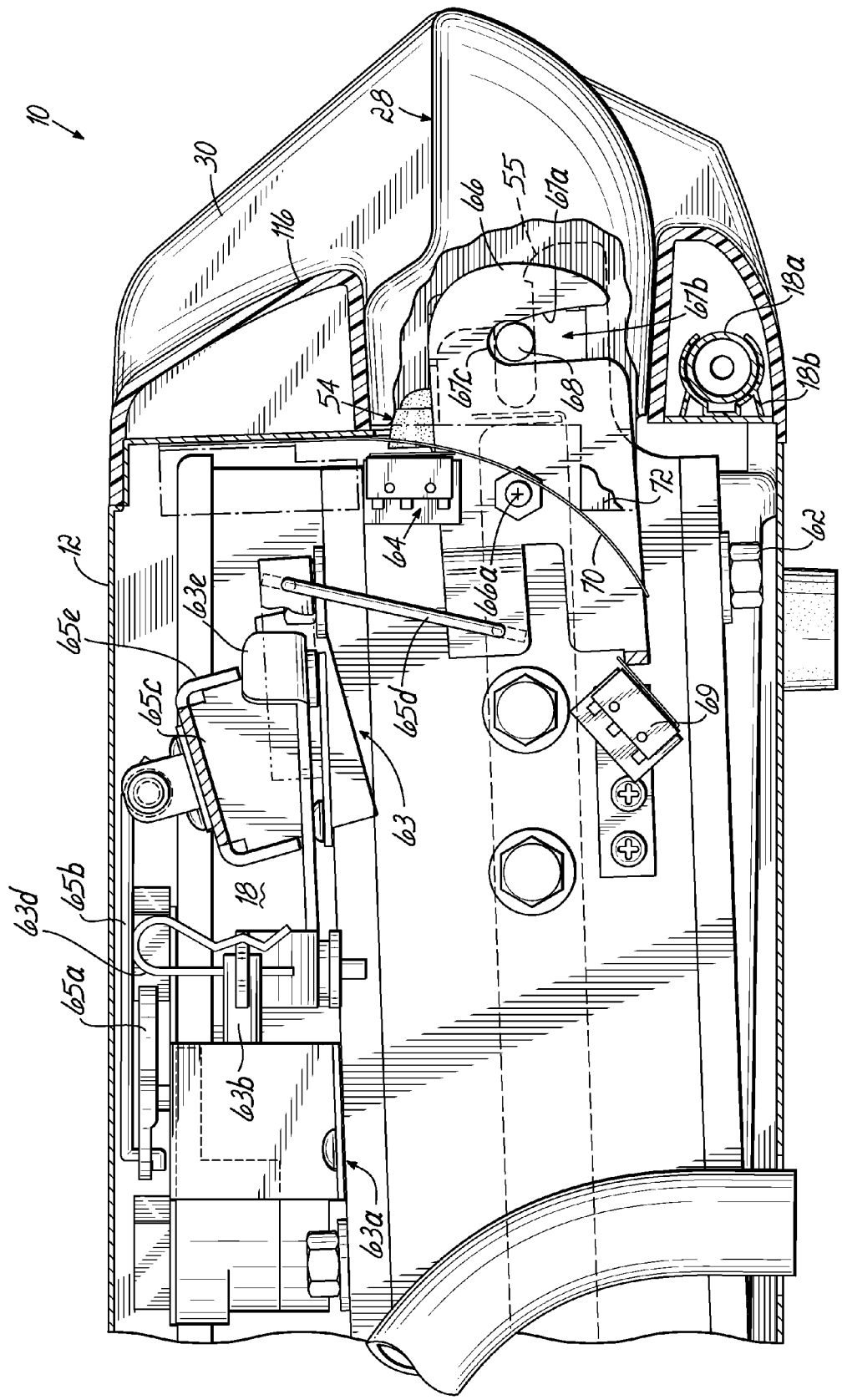
FIG. 5C is a view similar to FIG. 5A illustrating a portion of a pressure interlock assembly of the sterilizer of FIGS. 1-3.

With reference to FIGS. 4-5C, a motorized locking assembly 63 is mounted on the main housing 60 of the sterilizer 10 and works in cooperation with a handle portion sensor assembly 64 to hold the handle portion 28 in sealing engagement with the cavity portion 38. The motorized locking assembly 63 includes a motor 65 that is operatively connected, in ways known to those of ordinary skill in the art, to one or more engaging members configured to engage corresponding elements on the handle portion 28. In the exemplary embodiment of FIGS. 4-5B, the engaging members are in the form of a pair of claws 66 that include respective slots 67 engageable with a cylindrically shaped elongate locking member 68 fixed to and extending through the handle portion 28 and having end portions laterally protruding from the support block 57 of the handle portion 28. Persons of ordinary skill in the art will, however, readily appreciate that any number and type of engaging members and corresponding locking elements in any number and of any type can be substituted for the exemplary claws 66 and elongate locking element 68 of this exemplary embodiment.

The claws 66 are rotatable about a common axis such that motorized rotation of claws 66 about such axis causes the claws 66 to engage the elongate locking element 68, thereby preventing movement of the handle portion 28 away from the cavity portion 38 and housing 60. More particularly, rotation of the motor 65 in a first direction e.g., clockwise, causes rotation of an actuating arm 65a connected to the motor 65. Rotation of the actuating arm 65a, in turn, causes movement of a first link member 65b, a locking bracket 65c and second link members 65d (only one shown for ease of understanding) that are coupled to corresponding ends of each of the claws 66. Rotation of each of the claws 66 causes a re-orientation of a corresponding slot 67 from a generally horizontal orientation to a vertical one, which thereby restricts movement of the locking element 68. Rotation of the motor 65 in a second direction e.g., counter-clockwise reorients the slot 67 back to the generally horizontal orientation, such that the locking element 68 is unrestricted from movement associated with decoupling of the handle portion 28 from the cavity portion 38. In one aspect of this embodiment, reversal of the direction of rotation of motor 65 between the clockwise and counter-clockwise directions may be facilitated, for example and without limitation, by a wig-wag type solenoid mechanism. In yet another aspect of this embodiment, the locking element 68 may include one or more bushings (not shown) to facilitate engagement thereof with the claws 66. More particularly, the one or more bushings allow the claws 66 to roll over the bushings to facilitate the engagement.

With continued reference to FIGS. 4-5C, and in one aspect of the exemplary embodiment of the motorized locking assembly 63, each of the slots 67 of the claws 66 includes a biasing surface 67a connecting an entrance portion 67b of the slot 67 with a coupling portion 67c thereof. Rotation of the claw 66 urges motion of the locking element 68 from the entrance portion 67b, along the biasing surface 67a and toward the coupling portion 67c. This relative motion of the locking element 68 with respect to the axis of rotation 66a of the claws 66 moves the handle portion 28, to which the locking element 68 is connected, into sealing engagement with the cavity portion 38 of the pressure chamber 14. Moreover, rotation of the claws 66 may be suitably restricted, for example, via one or more limit switches 69 suitably positioned to cause an interruption of the energy driving the motor 65 of the motorized locking assembly 63.

As mentioned above, the motorized locking assembly 63 cooperates with a handle portion sensor assembly 64 to hold the handle portion 28 in sealing engagement with the cavity portion 38. The sensor assembly 64 detects a position of the handle portion 28 such that, if the handle portion 28 is in a position of engagement with the cavity portion 38, actuation of the motorized locking assembly 63 will be permitted. In the exemplary embodiment of FIGS. 5A-B, the sensor assembly 64 is in the form of a spring-loaded contactor 70 that is actuated (i.e., causes a corresponding electrical circuit to be closed) by a cooperating probe 72 attached to the handle portion 28. Alternatively, the sensor assembly 64 may be of any type other than described above, and be present in any number, so long as it permits actuation of the motorized locking assembly 63 when the handle portion 28 is in an expected position. Alternatively also, a sterilizer 10 may include no handle portion sensor assembly at all.

With continued reference to FIGS. 4-5C, a secondary locking mechanism in the form of a pressure interlock assembly 63a prevents the handle portion 28 from moving away from housing 60 while the chamber 14 is pressurized. The pressure interlock assembly 63a fluidly communicates with the pressure chamber 14 and with the steam management assembly 16 such that when the pressure within the chamber 14 reaches, for example, between about 1 and about 2 psi, a piston 63b thereof begins to extend. Moreover, the interlock assembly 63a may be such that when pressure within the chamber 14 reaches about 6 psi, the piston 63b is fully extended (FIGS. 5A, 5C) such as to engage one or more of components of motorized locking assembly 63, thereby preventing unlocking motion thereof.

In this exemplary embodiment, the piston 63b is coupled, at a distal end thereof, and through a clip 63d, to a bracket 63e. Bracket 63e is positioned to engage a front plate 65e of the locking bracket 65c of motorized locking assembly 63. Once steam vents and the pressure within chamber 14 returns to preset levels (e.g., less than about 6 psi), the piston 63b returns to its original position (FIG. 5B), thereby permitting unlocking motion of components of motorized locking assembly 63, which in turn allows separation of handle 28 from housing 60. A check valve (not shown) may fluidly communicate the pressure interlock assembly 63a and the boiler 92 and prevent the pressure chamber 14 from drawing water from the water reservoir 18 when the chamber 14 cools down in case of an abnormal shut-down where the handle portion 28 does not separate from housing 60.

Referring again to FIGS. 2-3B, and as described above, the handle portion 28 is releasably coupled to a tray 32 configured to hold surgical or dental instruments to be sterilized. To that end, the tray 32 in the illustrative embodiment of FIG. 2 is in the form of an open-top tray such that access to the instruments is readily available upon removal of the tray 32 from within the cavity portion 38, thereby obviating any additional steps (e.g., opening a two-part clam-like tray). The open-top tray includes a bottom plate 74, an end wall 76, and opposed lateral walls 78. The open-top tray 32 includes apertures to facilitate the flow of steam from the pressure chamber 14 and onto the surfaces of the instruments. Thus, a first set of apertures 80 is disposed on the bottom plate 74 such as to maximize contact of the instruments resting on the bottom plate 74 with steam in the pressure chamber 14. Similarly, a second set of apertures 82 is disposed on the end wall 76 and lateral walls 78. Alternatively, each of the end wall 76 and lateral walls 78 may include apertures 82 of any shape other than depicted or include no apertures at all.

In addition to steam-flowing considerations, the apertures 80, 82 are suitably chosen such that integrity of the walls 74, 76, 78 can be maintained after repeated use of the tray and in light of the high-pressure environment in to which they are exposed during normal sterilization cycles. In one advantageous aspect of the embodiment of FIG. 2, the sliding guides 50 provide spacing between the bottom plate 74 and the bottom wall 40 of the cavity portion 38, thereby facilitating flow of steam through the apertures 80.

With continued reference to FIGS. 2-3B, coupling of the handle portion 28 with the tray 32 provides a convenient method to selectively insert and remove the tray 32 respectively into or from other portions of the pressure chamber 14 disposed within the sterilizer 10. The handle portion 28 is releasably coupled to the tray 32 such that it can be readily separated therefrom, for example, if the tray 32 needs to be replaced. The exemplary embodiment depicted in FIGS. 3A-B shows the handle portion 28 being coupled to the tray 32 via a pair of wing nuts 83 that engage a pair of threaded members 83a protruding from the block support 57 of the handle portion 28. Persons of ordinary skill in the art will readily appreciate, however, that any suitable type of fastener in any suitable number may be employed instead to provide releasable intercoupling of the handle portion 28 and tray 32.

The tray 32 may be configured to receive, in addition to freely-moving instruments, a cassette 84 (shown in phantom) holding a predetermined set of surgical or dental instruments. The exemplary cassette 84 depicted in FIG. 2 includes six walls having cassette apertures 86 adapted to let steam flow through them. The apertures 80 (i.e., the first set of apertures) disposed on the bottom plate 74 of the tray 32 are shaped and dimensioned such that flow of steam is not hindered from the pressure chamber 14, through the apertures 80 and through the cassette apertures 86.

Although the apertures 80 are exemplarily depicted as shown, persons of ordinary skill in the art will appreciate that apertures 80 in any number may be shaped and arranged in any suitable form, so long as they do not hinder the flow of steam through the cassette apertures 86, to thereby facilitate sterilizing of the instruments held therein. The apertures 82 disposed on the end and lateral walls 76, 78 of the tray 32 (i.e., the second set of apertures) further facilitate sterilizing of the instruments held in the cassette 84. The apertures 82 permit multi-directional flow of steam from the pressure chamber 14 through the cassette apertures 86.

Referring again to FIGS. 3-4, sterilizing of the instruments is carried out by injecting and evacuating pressurized steam into and from the pressure chamber 14. To this end, a steam inlet 88 and a steam outlet 90 extend through the rear wall 44 and are each in fluid communication with a steam management assembly 16, with which steam is selectively exchanged. A temperature sensor (not shown), such as an RTD-type sensor may also extend through the rear wall 44 to detect the temperature of steam within the chamber 14. The steam management assembly 16 includes a boiler 92 providing a source of steam to the pressure chamber 14. The boiler 92 heats up clean water received from a boiler pump 94 and feeds it into the pressure chamber 14 through a boiler conduit 96, and the steam inlet 88. A relief valve 92a may further be included to provide pressure relief to the boiler 92. In this exemplary embodiment, moreover, a plastic housing 92b surrounds and protects a large portion of relief valve 92a, although this is intended to be illustrative rather than limiting.

The steam management assembly 16 further includes a vent valve 98 in the form of a solenoid configured to open and close to permit the flow of air and/or steam therethrough. Air flows from the pressure chamber 14 through the steam outlet 90, vent conduit 100, and through the vent valve 98 when displaced by steam being injected into the pressure chamber 14. Similarly, steam flows from the pressure chamber 14 and through the steam outlet 90, vent conduit 100, and vent valve 98 when steam is evacuated at or near the end of a sterilizing cycle. Moreover, a secondary conduit 98a may communicate steam management assembly 16 with a pressure transducer (not shown) on the control module 24, to thereby permit feedback as known by those skilled in the art. Other parts of the exemplary steam management assembly 16 are taught in U.S. Pat. No. 6,984,359, assigned to the assignee of the present invention, and the disclosure of which is herein incorporated by reference in its entirety.

Referring again to FIGS. 3-3A, steam pressurized within the pressure chamber 14 to carry out the sterilization of instruments causes an expansion of the chamber 14 such that an outward deformation of the walls 40, 42, 44 of the chamber 14 is observed. This outward deformation, which may otherwise cause undesirable movement of the chamber 14 within the main housing 60 of the sterilizer 10, is advantageously used to secure the chamber 14 within the housing 60. More particularly, two thermal insulation assemblies 102 made, for example, of a non-conductive and rigid material such as plastic, are disposed between each of the top and bottom walls 40 of the cavity portion 38 and corresponding top and bottom walls 61 of the housing 60. Each of the thermal insulation assemblies 102 includes a structural plate 106 having a plurality of pins 108 and a plurality of fins 110 respectively disposed on each of opposed faces of the structural plate 106. The pins 108 on each thermal insulation assembly 102 are positioned to contact one of the top or bottom walls 61 of the housing 60, while the fins 110 are positioned to contact one of the top and bottom walls 40 of the cavity portion 38 of the pressure chamber 14.

When steam pressure builds up within the chamber 14, the top and bottom walls 40 of the cavity portion 38 deform, causing contact to be made respectively between the fins 110 and walls 40 of the cavity portion 38 and between the pins 108 and walls 61 of the housing 60. The non-conductive yet rigid nature of the material defining the thermal insulation assembly 102 permits the transfer of force between the pressure chamber 14 and the housing 60 while minimizing the conductive loss of heat from the chamber 14 to the housing 60. The force transfer frictionally holds the cavity portion 38 in place within the housing 60, preventing any translational motion thereof with respect to the housing 60. Moreover, a normal force exerted by the housing 60 through the thermal insulation assembly 102 against the walls 40 of the cavity portion 38 refrains further expansion (i.e., deformation) of the cavity portion 38.

While the embodiment of FIGS. 3-3A includes one thermal insulation assembly disposed adjacent each of the top and bottom walls 40 of the cavity portion 38, it is contemplated that thermal insulation assemblies 102 in any number may be alternatively disposed adjacent one, both or none of the walls 40 of the cavity portion 38. Similarly, any suitable configuration of a structure capable of frictionally holding the cavity portion 38 within the housing 60 may be substituted for the exemplary thermal insulation assembly 102 described above.

With continued reference to FIGS. 3-3A, and as described above, steam is evacuated from the pressure chamber 14 at or near the end of a sterilizing cycle by being sequentially directed through the steam outlet 90, vent conduit 100 and vent valve 98. Although steam is substantially evacuated at or near the end of the sterilizing cycle, the reduced pressure gradient between the pressure chamber 14 and points along the vent valve 98 results in some steam remaining within the pressure chamber 14 at or near the end of the sterilizing cycle, thus requiring additional drying of the contents within the chamber 14. To this end, a heating element in the form of a flat heating blanket 112 is disposed on and made to contact the respective exterior surfaces 114 of the top and bottom walls 40 of the cavity portion 38.

The flat heating blankets 112 are actuated at about the end of a sterilizing cycle to conductively transfer heat therefrom and onto the walls 40. Heat from the walls 40 is then convectively transferred onto the instruments within the chamber 14 to thereby dry them. In one aspect of this embodiment, the sterilizing cycle may be such that the handle portion 28 is manually or automatically decoupled from the cavity portion 38 such that steam can escape through the opening 48 and out of the cavity portion 38. Heat from the flat heating blanket 112 may also be such that it causes a positive pressure differential from the interior portion 46 of the cavity portion 38. Advantageously, this positive pressure differential prevents the flow of air from the environment surrounding the sterilizer 10 and into the cavity portion 38, which would otherwise potentially contaminate the sterile instruments.

With continued reference to FIGS. 3-3A, in another advantageous aspect of the above embodiment, the exterior location of the flat heating blankets 112 with respect to the cavity portion 38 permits drying of the contents thereof without occupying any of the volume defined by the interior portion 46, therefore maximizing the instrument-holding capacity of the pressure chamber 14.

While the embodiment of FIGS. 3-3A depicts two flat heating blankets 112 each respectively disposed against the exterior surface 114 of each of the top and bottom walls 40, it is contemplated that heating elements of any type, shape and in any number may be disposed on one, both or neither of the top and bottom walls 40. Similarly, it is contemplated that other walls such as the sidewalls 42 and/or rear wall 44 of the cavity portion 38 may include such heating elements.

Referring again to FIGS. 2-5A, and as described above, drying of the instruments held within the cavity portion 38 at about the end of a sterilizing cycle may include decoupling of the handle portion 28 from the cavity portion 38. Such decoupling may result, at least temporarily, in the deposit of condensed steam from the pressure chamber 14 on portions of the front face 30 of the sterilizer 10. The return of condensed steam (i.e., in the form of water) into the cavity portion 38, after sterilization, may not be desirable. To address this need, the front face 30 of the sterilizer 10 includes a contoured portion 116 configured to direct condensed steam thereon away from the cavity portion 38. Moreover, a heating element in the form of a heating strip 117 is operatively connected to the control module 24 and disposed behind the front face 30 of the sterilizer 10. The heating strip 117 transfers heat onto the contoured portion 116 to cause evaporation of the condensed steam deposited on contoured portion 116. The contoured portion 116 and heating strip 117 thus jointly provide redundant components to prevent condensed steam from returning into the cavity portion 38.

While the contoured portion 116 and heating element in the form of a heating strip 117 are depicted as shown, persons of ordinary skill in the art will readily appreciate that, alternatively, only one of the redundant components may be present. Further, a heating element in any number, of any suitable type and disposed anywhere in the sterilizer 10 as well as a contoured portion of any shape may be respectively substituted for the heating strip 117 and contoured portion 116 of FIGS. 2-5A.

Referring again to FIGS. 1-4, and as described above, the sterilizer 10 uses steam to sterilize the instruments within the pressure chamber 14. The steam is fed into the pressure chamber 14 from a steam source such as the exemplary boiler 92 described above. The boiler, in turn, requires a supply of clean water which it then converts into steam. To this end, the sterilizer 10 includes a water reservoir 18 within the outer casing 12, which is in fluid communication with the boiler 92 to supply clean water thereto. The exemplary water reservoir 18 of FIGS. 1-4 is irregularly shaped and defines a water-holding volume suitably chosen to permit one or more sterilizing cycles before requiring replenishment thereof.

Figure 6:
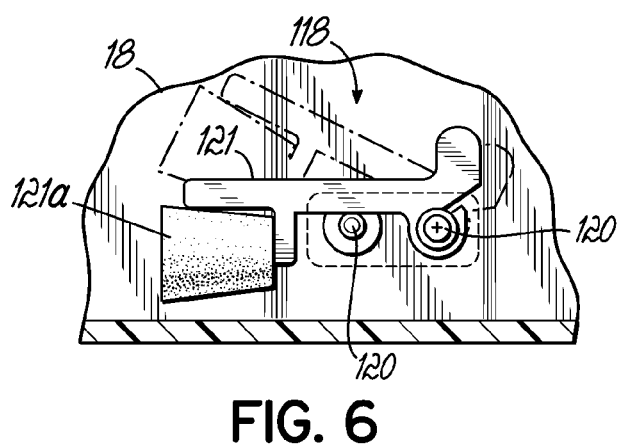
FIG. 6 is an enlarged view of a sensor assembly of the sterilizer of FIGS. 1-3.

With reference to FIG. 6, the water reservoir 18 may include one or more suitably located sensors operatively connected to the control module 24. In the illustrative embodiment of FIG. 6, a dual-function sensor 118 is configured to detect the level and a quality characteristic of the clean water in the reservoir 18 such that it may, for example, and through a signal to the control module 24, impede the start of a sterilization cycle if a condition, such as a predetermined level of water, is met. Moreover, the dual-function sensor 118 is configured to detect a quality characteristic of the water in the reservoir 18 such as, and without limitation, the parts per million of an undesirable substance or water hardness levels. The dual-function sensor 118 may be further configured, and through a signal to the control module 24, to impede the start of a sterilization cycle if a condition, such as a predetermined level of a substance in the water, is met.

In the exemplary embodiment of FIG. 6, the sensor 118 includes two probes 120 such that a flow of electrical current between the two probes 120 is measured and such measurement linked to a predetermined quality characteristic of the water therein. Similarly, the two probes 120 are capable of closing a circuit when an electrical bridge member 121 contacts the two probes 120. More particularly, the bridge member 121 is rotatably coupled, at one end, to one of the two probes, and is further coupled to a float such as a cork 121a having a density lower than water. When the level of water in the reservoir 18 is sufficiently low, the vertical position of the cork 121a drops, thereby permitting the bridge member 121 to contact both probes 120, thus closing a circuit. Closing of the circuit sends a signal to the control module 24, as explained above.

Figure 6A:
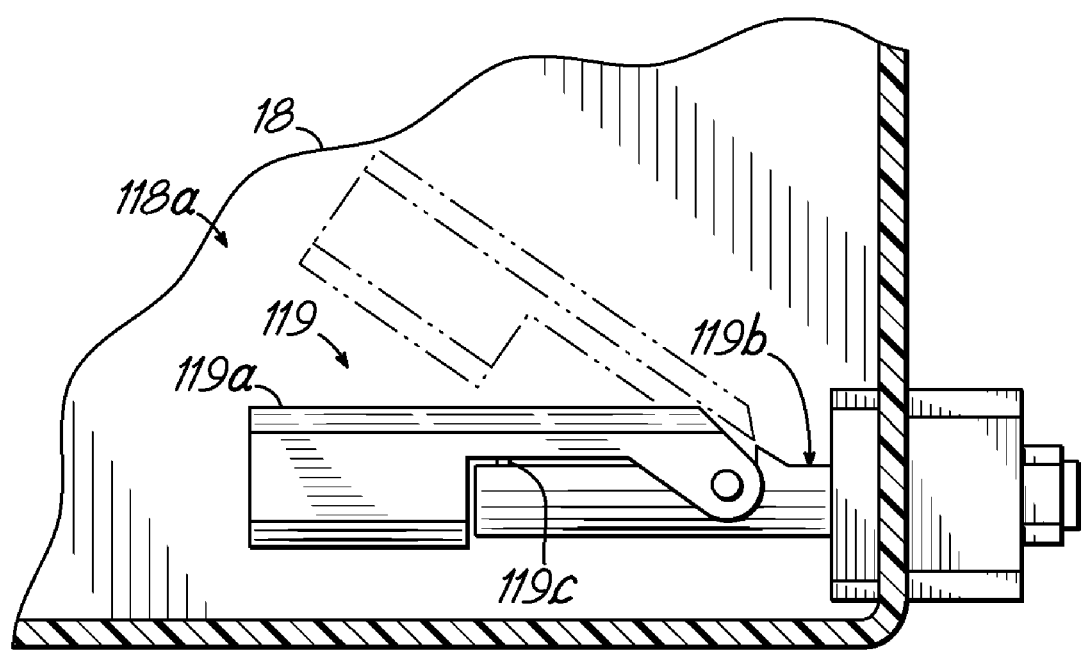
FIG. 6a is an enlarged view of another embodiment of a sensor assembly that may be used with the sterilizer of FIGS. 1-3.

While this exemplary embodiment depicts a dual-function sensor 118, those of ordinary skill in the art will readily appreciate that, alternatively, the water reservoir 18 may include other types of sensors or even be configured to measure only one of the level of clean water or a quality characteristic thereof. For example, and with particular reference to FIG. 6a, an alternative embodiment of a sensor 118a is configured to sense the level of water in water reservoir 18. Sensor 118a includes a float 119 that rises or drops with the level of water. Float 119 is operatively coupled, through link element 119a, to an assembly 119b that is operatively connected to control module 24. Movement of float 119 and link element 119a between the two shown positions (in solid and phantom respectively) engages and disengages from an actuator 119c which in turn opens and closes a circuit (not shown) within assembly 119b. Closing of the circuit, in turn, permits a corresponding signal to be sent to control module 24.

Referring again to FIGS. 1, 4, the water reservoir 18 includes an opening 122 that provides access to the interior of the reservoir 18. The opening 122 is used to fill the reservoir 18 and may further be used for other purposes such as inspection of the contents of the reservoir 18, cleaning, or purging thereof. A funneling structure 124 is releasably coupled to and disposed about the opening 122 to facilitate the filling process and includes inwardly sloped surfaces 126 to direct water into the opening 122. The funneling structure 124 may be made of any suitable materials such as, and without limitation, plastics, glass, metal or composite materials. Moreover, a reservoir lid 125 is hingedly or frictionally coupled to the funneling structure 124 and disposed thereover to prevent debris and the like from accessing the contents of the water reservoir 18.

The funneling structure 124 includes an overflow channel 128 extending from a point proximate the opening 122 and away therefrom, to direct overflow water away from the water reservoir 18. The exemplary overflow channel 128 in the illustrative embodiment of FIG. 1 is generally linear, generally orthogonal to the perimeter of the opening 122, and extends to an edge 130 of the outer casing 12, although it is contemplated that alternate overflow channels having other shapes and extending to points other than depicted can be substituted for the exemplary channel 128.

Referring again to FIGS. 5A-B, in another aspect of this embodiment, the water reservoir 18 may further include a drain port (not shown) to evacuate water from the reservoir 18 if and when necessary. Drainage of the water is facilitated by a drain tube 18a fluidly coupleable to the drain port via fittings and the like known to those of ordinary skill in the art. In an advantageous aspect of this embodiment, the drain tube 18a may be stored along the front face 30 of the sterilizer 10, via support brackets 18b, for convenient retrieval thereof when needed.

Figure 7:
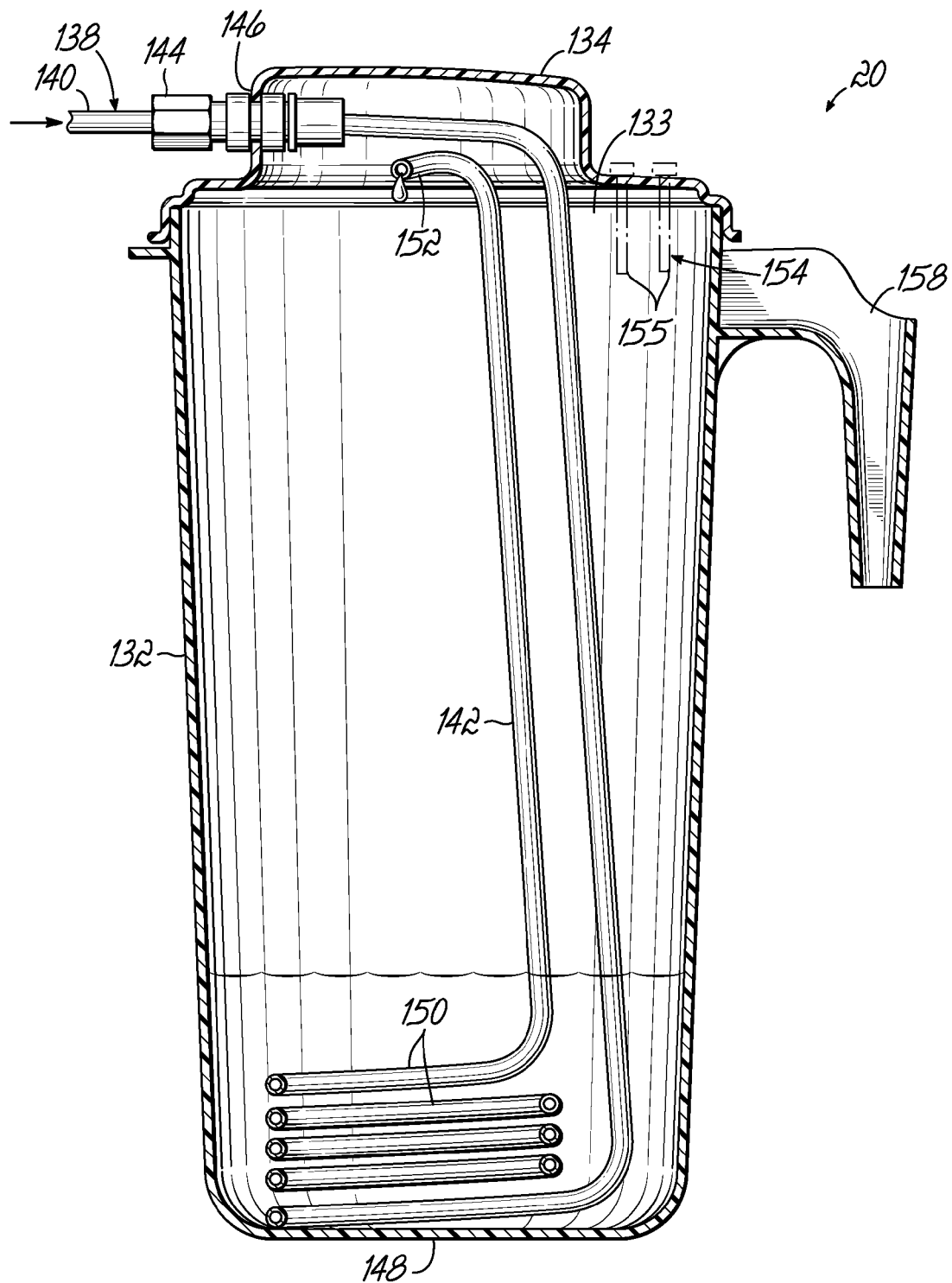
FIG. 7 is a cross-sectional view of an embodiment of a condensation container of the sterilizer of FIGS. 1-3.

With reference to FIGS. 1, 4, 7, and as described above, the water held in the water reservoir 18 is converted to steam by the boiler 92, an the steam is used to sterilize instruments held within the pressure chamber 14. At or near the end of a sterilization cycle, steam is directed away from the pressure chamber 14 through a valve 98 in ways and further through components as described above. Steam is then condensed and deposited into the external condensation tank 20 for later disposal.

Figure 8:
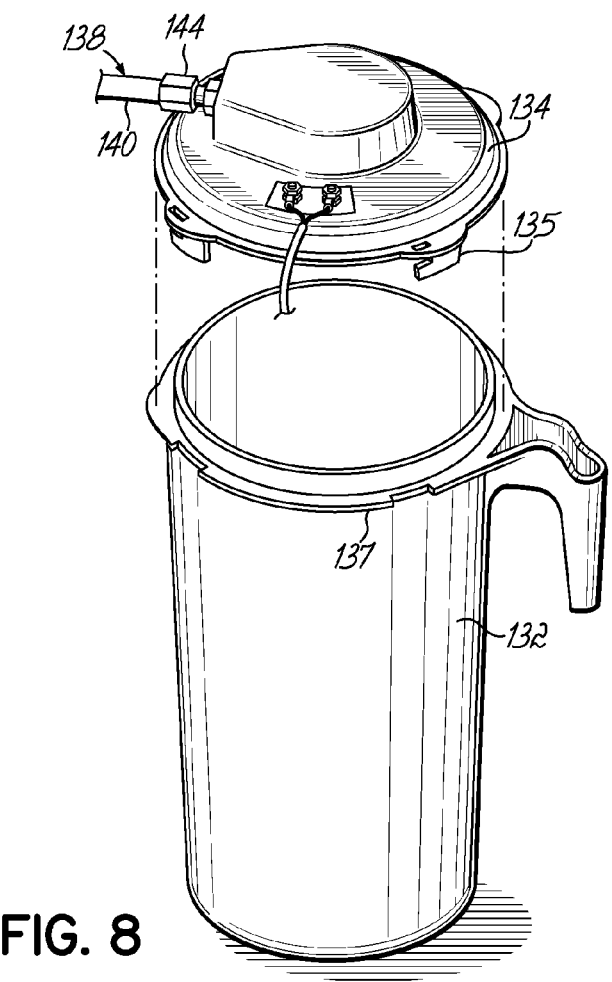
FIG. 8 is a perspective view of the container of FIG. 7 having the lid thereof removed from a main body of the container.
Figure 9:
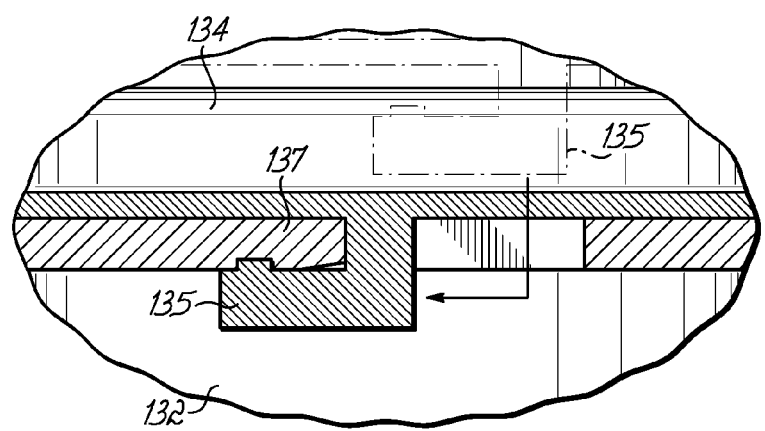
FIG. 9 is an enlarged cross-sectional view of a locking feature of the container of FIGS. 7-8 to one another.

With particular reference to FIGS. 7-9, the external condensation tank 20 includes a generally cylindrical main body 132 including a tank opening 133 and a lid 134 releasably coupled thereto about the tank opening 133. The tank opening 133 provides access to an interior of the main body 132 such that, among other things, wastewater therein can be poured out. The lid 134 is substantially non-rotationally held by the main body 132 such that rotation of a wastewater conduit 138 coupled to the lid 134 is not required, which would otherwise expose portions of the conduit 138 to unnecessary bending. In the illustrative embodiment of FIGS. 7-9, the lid 134 is a snap-on type, such that coupling requires snapping the lid 134 onto the main body 132 to move them into engagement with one another. Alternatively, other suitable methods or components permitting substantially non-rotational coupling of the lid 134 and main body 132 may be substituted. For example, and without limitation, the lid 134 may be coupled to the main body 132 via clamps or fasteners (not shown).

In this illustrative embodiment, moreover, coupling between the lid 134 and the main body 132 includes engaging one or more discrete elements in the form of protruding elements or teeth 135 of the lid 134 with one or more cooperating recesses or engaging surface 137 of the main body 132. Accordingly, coupling of the lid 134 onto the main body 132 includes a slight rotation, for example of no more than about 5 degrees, of the lid 134 relative to the main body 132.

While this embodiment shows the protruding elements 135 forming part of the lid 134 and the engaging surfaces 137 being part of the main body 132, it is contemplated that the protruding elements 135 may instead be part of the main body 132 while the engaging surfaces are part of the lid 134. Alternatively, it is also contemplated that each of the lid 134 and the main body 132 may have both types of locking features (e.g., one or more protruding elements 135 and one or more engaging surfaces 137) cooperating with like features on the other of the lid 134 and main body 132.

The wastewater conduit 138 includes a flexible tubing portion 140 in fluid communication with a coil portion 142, both interconnected via one or more suitable components such as, and without limitation, compression fittings (not shown). The wastewater conduit 138 is coupled to the lid 134 such that the flexible tubing portion 140 lies generally outside the external condensation tank 20 while the coil portion 142 lies within it. In another aspect of this embodiment, the wastewater conduit 138 is coupled to the lid 134 such that the flexible tubing and coil portions 140, 142 do not slide or bend with respect to the lid 134, thereby minimizing the likelihood of damage to either portion 140, 142 of the wastewater conduit 138. In the illustrative embodiment of FIGS. 1, 7, a coupling member 144 is fixedly coupled to a vertically oriented wall 146 (i.e., orthogonal to a base 148 of the main body 132) of the lid 134 and provides connecting points for both portions 140, 142 of the wastewater conduit 138.

With continued reference to FIGS. 7-9, the flexible tubing portion 140 transfers steam evacuated from the pressure chamber 14 (FIG. 1) and directs it to the coil portion 142. The flexible tubing portion 140 may be made of any material that provides some level of flexibility to thereby provide for motion of the condensation tank 20 away from and toward other portions of the sterilizer 10. Further, the material must be suitably chosen such that the integrity of the flexible tubing portion 140 can be maintained in light of the exposure to relatively high temperature steam. Thus, the flexible tubing portion 140 may include, without limitation, braided metal wire, plastics, rubber or rubber-like composites.

The coil portion 142 receives steam from the flexible tubing portion 140 and routes the steam through a heat exchanging operation to reduce the temperature thereof and convert it into water. To this end, the coil portion 142 is an elongate tubing member including several coiled loops 150 to maximize exposure to water already in the external condensation tank 20. In operation, heat from the steam within the coil portion 142 is convectively transferred to water in the tank 20, thereby reducing the temperature of the steam. The coil portion 142 ends in a terminal portion 152 lying proximate a top portion of the tank 20 (i.e., proximate the lid 134) such that steam in the form of water exits the coil portion 142 therethrough and is deposited in the external condensation tank 20, for later disposal.

The coil portion 142 is made of copper or any other material suitable to withstand the high temperatures of steam while providing for suitable heat exchanging of the steam with surrounding wastewater in the external condensation tank 20.

The external condensation tank 20 may further include a level sensor 154 operatively coupled to the control module 24 and configured to detect a level of the wastewater therein. The sensor 154 may be further configured such that a sterilization cycle is not permitted if a condition, such as a predetermined level of wastewater, is detected by the sensor 154. While the exemplary level sensor 154 is depicted including two probes 155 coupled to the lid 134 and extending into the interior of the main body 132, as shown, any alternate type of level sensor positioned anywhere in the external condensation tank 20 is contemplated.

In another aspect of the illustrative embodiment of FIGS. 7-9, the external condensation tank 20 includes a handle 158 spaced from the main body 132. The spaced position of the handle 158 facilitates minimization of heat transfer from the wastewater in the condensation tank 20 and from the main body 132, thereby permitting comfortable manual transportation of the external condensation tank 20. The handle 158 is made of a suitably chosen material such that it minimizes conductive heat transfer from the main body 132 and such that it can sustain the weight of the condensation tank 20 when filled.

Referring again to FIG. 1, an alternate embodiment of an external condensation tank may include a pump assembly 162 operatively connected to the main body 132 and to a drain 166 or similar dumping site. The pump assembly 162 and drain 166 are diagrammatically depicted in phantom for ease of understanding. In this alternative embodiment, wastewater can be selectively directed from the external condensation tank 20, thereby obviating the need to manually pour the contents thereof into a drain or the like.

Accordingly, many further embodiments, applications and modifications of the invention will become readily apparent to those of ordinary skill in the art without departing from the scope of the invention which is intended to be bound only by the claims appended hereto.

What is claimed is:

1. A portable steam sterilizer for surgical instruments comprising:
   a tray configured to hold the instruments;
   a pressure chamber including:
     a cavity portion, said cavity portion including a plurality of walls, said cavity portion being configured to releasably receive said tray, and
     a handle portion coupled to said tray for selectively inserting and removing said tray respectively into and from within said cavity portion, said handle portion being sealingly engageable with said cavity portion to thereby define said pressure chamber, said handle portion comprising a sealing member that deforms to seal against at least one of said plurality of walls of said cavity portion when said pressure chamber is filled with pressurized steam;
   a steam inlet fluidly communicating said pressure chamber with a source of steam to selectively permit steam to flow from said source into said pressure chamber;
   a steam outlet fluidly communicating said pressure chamber with a steam management assembly to selectively permit steam to flow from said pressure chamber into said steam management assembly; and
   at least one heating element disposed on an outer face of at least one of said plurality of walls.

2. The portable steam sterilizer of claim 1 wherein the sealing member comprises a resilient gasket member releasably coupled to said handle portion, sealingly engageable with said cavity portion, and configured to prevent steam from flowing out of said pressure chamber.

3. The portable steam sterilizer of claim 2, wherein said gasket member includes a channel, said channel being configured to deform when filled with steam, to thereby bring said handle portion into sealing engagement with said cavity portion.

4. The portable steam sterilizer of claim 1, wherein said handle portion is releasably coupled to said tray.

5. The portable steam sterilizer of claim 1, further comprising:
a main housing including a thermal insulation assembly, said assembly being disposed to contact at least one of said plurality of walls to frictionally hold said pressure chamber within said housing.

6. The portable steam sterilizer of claim 1, further comprising:
a main housing, said housing including at least two walls interconnected by fasteners.

7. The portable steam sterilizer of claim 1, wherein said at least one heating element is configured to dry an interior portion of said pressure chamber when a substantial portion of the steam has been evacuated from said pressure chamber at about an end of a sterilizing cycle.

8. The portable steam sterilizer of claim 7, wherein said at least one heating element is further configured to dry said interior portion when said handle portion is decoupled from said cavity portion.

9. The portable steam sterilizer of claim 8, wherein said at least one heating element is further configured to create a positive pressure flow from said interior portion.

10. The portable steam sterilizer of claim 1, further comprising:
a motorized locking assembly configured to hold said handle portion in sealing engagement with said cavity portion.

11. The portable steam sterilizer of claim 10, wherein said locking assembly comprises:
at least one elongate locking element extending laterally from said handle portion; and
a motor operatively coupled to at least one engaging member, said engaging member being configured to engage said at least one elongate locking element.

12. The portable steam sterilizer of claim 10, further comprising:
a sensor assembly operatively coupled to said locking assembly and being configured to detect a position of said handle portion to thereby permit actuation of said locking assembly.

13. The portable steam sterilizer of claim 10, further comprising:
a secondary locking assembly configured to engage said motorized locking assembly to prevent separation between said handle portion and said cavity portion when a predetermined level of pressure is present within said pressure chamber.

14. The portable steam sterilizer of claim 1, wherein:
said tray comprises at least one generally vertically-oriented wall, said vertically-oriented wall including a first plurality of apertures configured to let steam flow therethrough; and
said tray is configured to hold a surgical instrument cassette thereon, said cassette including a second plurality of walls and a second plurality of apertures disposed on at least one of said second plurality of walls, said second plurality of apertures being configured to let steam flow therethrough;
wherein said first plurality of apertures is configured such that a flow of steam is not substantially hindered through said second plurality of apertures.

15. A pressure chamber for use within a portable steam sterilizer for surgical instruments comprising:
a cavity portion, said cavity portion including a plurality of walls, said cavity portion being configured to releasably receive a tray holding the instruments;
a handle portion sealingly engageable with said cavity portion to thereby define said pressure chamber, said handle portion comprising a sealing member that deforms to seal against at least one of said plurality of walls of said cavity portion when said pressure chamber is filled with pressurized steam;
a steam inlet adapted for fluidly communicating said pressure chamber with a source of steam to selectively permit steam to flow from the source of steam into said pressure chamber;
a steam outlet adapted for fluidly communicating said pressure chamber with a steam management assembly to selectively permit steam to flow from said pressure chamber into the steam management assembly; and
at least one heating element disposed on an outer face of at least one of said plurality of walls;
wherein said handle portion is configured to releasably couple to the tray.

16. The pressure chamber of claim 15 wherein the sealing member comprises a resilient gasket member releasably coupled to said handle portion, sealingly engageable with said cavity portion, and configured to prevent steam from flowing out of said pressure chamber.

17. The pressure chamber of claim 16, wherein said gasket member includes a channel configured to deform when filled with steam to thereby bring said handle portion into sealing engagement with said cavity portion.

18. The pressure chamber of claim 15, wherein said at least one heating element is configured to dry an interior portion of said pressure chamber when a substantial portion of the steam has been evacuated from said pressure chamber at about an end of a sterilizing cycle.

* * * * *